United States Patent [19]

Cordon

[11] 4,075,316
[45] * Feb. 21, 1978

[54] DENTIFRICES

[75] Inventor: Martin Cordon, Highland Park, N.J.

[73] Assignee: Colgate-Palmolive Company, New York, N.Y.

[*] Notice: The portion of the term of this patent subsequent to May 4, 1993, has been disclaimed.

[21] Appl. No.: 662,068

[22] Filed: Feb. 27, 1976

Related U.S. Application Data

[63] Continuation of Ser. No. 561,842, March 25, 1975, Pat. No. 3,957,968, which is a continuation-in-part of Ser. No. 389,826, Aug. 20, 1973, abandoned, which is a continuation-in-part of Ser. No. 355,365, April 30, 1973, abandoned.

[51] Int. Cl.$^2$ ............................................. A61K 7/16
[52] U.S. Cl. .................................... 424/49; 424/52; 424/54; 424/57
[58] Field of Search .................................. 424/49–58

[56] References Cited

U.S. PATENT DOCUMENTS

| | | | |
|---|---|---|---|
| 2,010,910 | 8/1935 | Atkins | 424/49 |
| 3,060,098 | 10/1962 | Gershon | 424/57 |
| 3,121,623 | 2/1964 | Nesin | 51/293 |
| 3,151,027 | 9/1964 | Cooley et al. | 424/49 |
| 3,325,368 | 6/1967 | Wood | 424/52 |
| 3,662,059 | 5/1972 | Wiesner et al. | 424/52 |
| 3,689,637 | 9/1972 | Pader | 424/52 |
| 3,885,029 | 5/1975 | Norfleet et al. | 424/57 |
| 3,906,090 | 9/1975 | Colodney | 424/52 |
| 3,935,306 | 1/1976 | Roberts et al. | 424/49 |
| 3,954,961 | 5/1976 | Colodney et al. | 424/49 |
| 3,957,968 | 5/1976 | Cordon | 424/57 |

*Primary Examiner*—Shep K. Rose
*Attorney, Agent, or Firm*—Robert L. Stone; Murray M. Grill; Herbert S. Sylvester

[57] ABSTRACT

Dentifrices containing flat flakes of alpha-alumina.

5 Claims, No Drawings

DENTIFRICES

This application is a continuation of Ser. No. 561,842 filed Mar. 25, 1975, now U.S. Pat. No. 3,957,968 issued May 18, 1976 which is a continuation-in-part of Ser. No. 389,826 filed Aug. 20, 1973, now abandoned, which is a continuation-in-part of Ser. No. 355,365, filed Apr. 30, 1973 now abandoned, the entire disclosure of which is incorporated herein by reference.

This invention relates to dentifrices.

One aspect of this invention relates to a dentifrice having outstanding cleaning and polishing characteristics and containing a dental abrasive having a particle size of about 2 to 40 microns and a Mohs hardness of less than about 6 (e.g. 2 to 5) and a minor amount of flat flakes of alpha-alumina crystals, of disk- or plate-like configuration, said flakes having a mean (by weight) particle diameter of less than about 7 microns (e.g. about 2 to 7 microns).

The dentifrice is preferably substantially free of anhydrous alumina particles having diameters about 15 microns and thicknesses above about 2 microns. It will be seen that the "Linde C" alpha-alumina particles have smoothly rounded shapes, while the flat alumina particles have sharp edges indicating that they have been fractured perpendicular to their flat parallel faces. Generally the thicknesses of the flat flakes are less than about 1/3 (e.g. about 1/5 or 1/10) of their diameters, and are in the range of about 1/2 micron (or less) to about 2 microns (e.g. about 1 micron).

The flat alpha-alumina crystals, and a process for preparing them, are described in U.S. Pat. No. 3,121,623.

The presence of the flat alpha-alumina particles is found to impart improved tooth polishing and tooth cleaning and stain removal characteristics to the dentifrice. Also when they are used in highly flavored toothpastes, there is superior flavor retention even on long aging.

The proportion of the flat alumina particles in the dentifrice may be for instance, above 0.1% and less than 60% e.g. in the range of about 0.2 to 30%, preferably about 1 to 5%.

The dental abrasive of Mohs hardness less than about 6 may, for instance, be any of those conventionally empoloyed in toothpastes, such as hydrated alumina, anhydrous dicalcium phosphate, calcium pyrophosphate, insoluble sodium metaphosphate, dicalcium phosphate dihydrate, calcium carbonate, silica xerogels of the known high density or intermediate density types (such as those sold under the name Syloid 63 or Syloid 72 or Syloid 74), alkali metal or alkaline earth metal aluminosilicates (such as those having a refractive index of about 1.44-1.47, and containing at least about 70% silica, up to about 10% alumina, up to about 20% by weight of moisture and up to about 10% by weight of sodium oxide, the moisture content preferably being about 10-20% by weight, measured by loss at 1,000° C. and the typical content of sodium oxide being about 5-10% by weight), kappa-alumina (such as described in U.S. Pat. No. 3,003,919); synthetic resins (such as described in British Pat. No. 995,351); composite abrasive particles in which a hard mineral is coated with, or embedded in, a synthetic resin (the mineral being, for instance, crystalline silica, e.g., quartz, SiC, anhydrous alumina, hematite, zirconium silicate, etc. and the coating being, for instance, an impervious cross-linked thermoset synthetic resin such as melamine-formaldehyde resin, urea-formaldehyde, phenol-formaldehyde, or epoxy resins or polymers or copolymers of compounds having two or more polymerizable ethylenically unsaturated groups, e.g. diallyl phthalate polymers, such as described in U.S. Pat. No. 3,151,027).

The dental abrasive of Mohs hardness less than 6 and particle size about 2 to 40 microns may also be present in the form of relatively large agglomerates (of the individual particles) of such size as to be visible to the naked eye but easily reduced to the fine impalpable particle size upon being subjected to toothbrushing in the mouth. Such agglomerates are described in U.S. Pat. No. 3,574,823, for example, they may be agglomerated with or without binding agent which may be water-soluble or water-insoluble.

For most purposes it is preferable that the dental abrasive of Mohs hardness less than 6 have a particle size less than 20 microns to avoid any gritty feel.

The proportion of such dental abrasive in the dentifrice is usually in the range of about 10 to 60% and is preferably such that when the alpha alumina is omitted from the dentifrice, the RDA (radioactive dentin abrasion) is in the range of about 100 to 600, preferably about 100 or 200 to 450. Typically this proportion of dental abrasive is in the range of about 5 to 70% of the dentifrice, such as about 10 to 50%.

It is also within the broader scope of this invention to employ the alpha alumina flakes as the sole abrasive in the dentifrice, e.g. in concentrations of about 5 or 10 to 20%. In this case it is often desirable to include other solid ingredients, such as the finely divided thermoplastic polymers mentioned below, so as to provide a toothpaste of suitable consistency.

To make toothpastes or dental creams, the flat flakes of alpha-alumina and the other dental abrasives are dispersed in a dental vehicle which preferably contains a liquid which is water and/or a humectant such as glycerine, sorbitol, propylene glycol or polyethylene glycol 400, including suitable mixtures thereof. It is usually advantageous to use a mixture of both water and one or two humectants. Polyethylene glycols of higher molecular weight, e.g., polyethylene glycol 600 etc., may also be present. The total liquid content is generally well over 20% by weight of the vehicle (sorbitol, generally present in admixture with water, is considered as a liquid for this purpose). The preferred humectants are glycerine and sorbitol. Typically the vehicle contains about 0-80% by weight of glycerine, up to about 80% by weight of sorbitol and about 5 - 80% of water.

The vehicle usually also contains a thickening or gelling agent, such as the natural and synthetic gums and gum-like materials, such as Irish Moss, gum tragacanth, alkali metal (e.g. Li, K or Na) carboxymethyl cellulose and hydroxymethyl carboxyethyl cellulose, polyvinyl pyrrolidone, starch, water soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark by Laporte Industries, Ltd., and pectin or inorganic thickeners such as colloidal silica, e.g. synthetic finely divided silicas including those sold under the trademarks Cab-O-Sil M5, Syloid 244, Syloid 266 and Aerosil D200. The solid portion of the vehicle is typically present in an amount up to about 10% by weight of the toothpaste and preferably within the range of about 0.5-8% by weight.

Fine particles of thermoplastic resin may also be present, such as particles of solid polymer having a molecular weight above 1000 (and preferably above 10,000, e.g. about 10,000 to 100,000 or more) and a mean diameter less than about 50 microns (preferably in the range of about 0.5 to 50 microns, e.g., about 10 to 30 microns). The polymer particles may be prepared directly by emulsion or suspension polymerizing or by grinding the polymer in bulk, and may be present in amount of up to about 60% or more of the dentifrice, e.g. in the range of about 20 to 60%, such as about 20 to 50%, e.g. about 30 to 50% in a toothpaste. Examples of thermoplastic resins are polymerized ethylenically unsaturated compounds, such as polyolefines (e.g. polyethylene or polypropylene) or vinyl or vinylidene resins, such as polyvinyl chloride, polystyrene, vinyl chloride-vinyl acetate copolymers, styrene-butadiene copolymers, polyvinylidene chloride; polyamides such as nylon (e.g. nylon 6); cellulosics such as cellulose acetate, etc.

The toothpaste may also contain surface active agent, e.g. to achieve increased prophylactic action, assist in achieving thorough and complete dispersion of the instant compositions throughout the oral cavity, and render the instant compositions more cosmetically acceptable. The organic surface active material may be anionic, nonionic, ampholytic, or cationic in nature, and it is preferred to employ as the surface active agent a detersive material which imparts to the composition detersive and foaming properties. Suitable types of such detergents are water soluble salts of higher fatty acid monoglyceride monosulfates, such as sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1, 2 hydroxy propane sulfonates, and the substantially saturated higher aliphatic acyl amides of lower alphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of those compounds. The use of these sarcosine compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface active materials include nonionic agents such as condensates of sorbitan monostearate with approximately 60 moles of ethylene oxide, condensates of ethylene oxide with propylene oxide condensates of propylene glycol ("Pluronics") and amphoteric agents such as quaternized imidazole derivatives, which are available under the trademark "Miranol" such as Miranol $C_2M$. Cationic surface active germicides and antibacterial compounds such as di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure

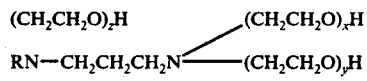

where R is a fatty alkyl group containing from about 12 to 18 carbon atoms, and x, y and z total 3 or higher, as well as salts thereof with mineral organic acids, may also be used. It is preferred that the total amount of surface-active agent be about 0.05 – 5% by weight, preferably about 1 – 3%, of the dentifrice.

Various other materials may be incorporated in the oral preparation of this invention. Examples thereof are coloring or whitening agents, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01 – 5%. Typical examples of such agents are guanidines, biguanides and amines such as:

$N^0$-(4-chlorobenzyl)-$N^5$-2,4-(dichlorobenzyl) biguanide;
p-chlorophenyl biguanide;
4-chlorobenzhdryl biguanide;
4-chlorobenzhydrylguanylurea;
$N^1$-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1, 3-bis (2-ethylhexyl)-5-methylhexahydropyrimidine; and their non-toxic acid addition salts.

Suitable flavoring or sweetening sialagogues may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate and saccharin. Suitably, flavor and sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride ($SnF_2 \cdot KF$), sodium hexafluorostannate, stannous chlorofluoride, sodium flurorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent, surface-active agent and flavor are then added. The toothpaste is then thoroughly deaerated (e.g. in vacuo) and tubed.

Preferably the amount of water-insoluble essential oil flavoring oil is above 0.5% and below 2%. Strongly flavored toothpastes contain above 1% of such flavoring oil, e.g. about 1.2 to 1.5%. The following Examples are given to illustrate this invention further. In this application all proportions are by weight unless otherwise indicated.

EXAMPLE 1

A toothpaste is prepared according to the following formulation: glycerine 22%; sodium carboxymethyl cellulose 0.80%; sodium benzoate 0.50%; sodium saccharin 0.20%; tetrasodium pyrophosphate 0.25%; dicalcium phosphate dihydrate 41.75%; dicalcium phosphate, anhydrous, 5.00%; alpha-alumina flakes, 5.00%, sodium lauryl sulfate, 0.975%; 35% aqueous solution of sodium N-lauroyl sarcosinate 2.00%; chloroform 3.30%; flavoring oil 1.30%; deionized water, balance. The alpha alumina flakes have a mean (by weight) particle diameter of about 4 microns, all the particles thereof have diameters less than 10.1 microns, about 85-95% (by weight) have diameters less than 6.0 microns and about 30-35% have particle diameters less than 3.5 microns. The dicalcium phosphates are both of standard dentifrice grade (e.g. about 15-20 microns average diameter). The toothpaste has an RDA of 366, a percent repolish of 62 and a percent stain removal of about 60. (An otherwise identical toothpaste containing none of the alumina flakes but containing 46.75% of the dicalcium phosphate dihydrate has an RDA of about 350, a percent repolish of 26 and a percent stain removal of about 60). It shows excellent flavor stability on aging at low and high temperatures.

EXAMPLE 2

Example 1 is repeated except that the amount of dicalcium phosphate dihydrate is 36.75% and the amount of dicalcium phosphate (anhydrous) is 10%. The toothpaste has an RDA of 471, a percent repolish of 66 and a percent stain removal of 76.

EXAMPLE 3

A toothpaste is prepared containing calcium carbonate (of about 4 to 5 microns mean particle size) and: (a) 5% of alpha-alumina flakes having a mean particle diameter of 5 microns, substantially all being less than about 12 microns in diameter, or (b) 2% of the same alumina flakes, or (c) 5% of the alpha-alumina flakes described in Example 1, or (d) 2% of the alpha-alumina flakes described in Example 1. The proportions of calcium carbonate are (a) 38%, (b) 41%, (c) 38%, (d) 41%. In each case the RDA is in the range of 400 - 435 and the percent repolish is high (e.g. about 57 - 58).

The formulation contains 22 parts glycerine, 0.9 part sodium carboxymethylcellulose, 0.5 part sodium benzoate, 0.2 part sodium saccharin, 26.45 parts deionized water, 0.2 part titanium dioxide pigment, 1 part flavor and 1.5 parts sodium lauryl sulfate.

EXAMPLE 4

To a transparent clear gel toothpaste containing 16% sodium aluminosilicate particles of relatively low abrasivity, 5% low density silica gel particles of about 4 micron average particle size (Syloid 244) there is added 2% of large, visible agglomerates of 150 to 450 microns particle size containing 20% polyethylene of about 1500 molecular weight and 80% alpha-alumina flakes having a mean particle diameter of 5 microns, substantially all being less than about 12 microns, in a toothpaste formulation as described below. The resulting speckled toothpaste shows a percent polish recovery of 38 and a percent stain removal of 64. In the absence of the speckles, the same toothpaste has a percent polish recovery of 24 and a percent stain removal of 41.

The composition of the sodium aluminosilicate may be expressed empirically as follows: silica about 72%; alumina about 8%; sodium oxide about 7%; water (Ignition loss at 1000° C) about 12%. It has a bulk density of about 0.19-0.22 g/cm$^3$, a surface area of 120 m$^2$/g, a particle size of about 2 microns (the particles being aggregates of material of ultimate particle size of 35 millimicrons), an oil absorption value of 150-160 g/100g and a pH (for a 4% slurry in water) of about 10.5.

The toothpaste formulation has the following composition, in addition to the ingredients named above. 25% glycerin, 0.5% sodium carboxymethyl-cellulose, 0.5 part sodium benzoate, 0.17 part sodium saccharin, 45% of a 70% aqueous solution of sorbitol, 0.8% of a 1% solution of coloring matter (F.D. & C. Red #2 plus F.D. & C. Yellow #6), 3% deionized water, 1% flavoring oil, 2% sodium lauryl sulfate, 1% chloroform. The silica gel and sodium aluminosilicate have indices of refraction about the same as that of the vehicle in which they are dispersed and the toothpaste is thus a clear gel.

EXAMPLE 5

A pearlescent toothpaste is prepared containing 16% of sodium aluminosilicate particles of Example 4, 4% of low density silica gel particles (as in Ex. 4), 1% of pearlescent flakes of 15 to 40 micron particle size, and 1% of (a) alpha-alumina flakes having a mean particle diameter of 5 microns, substantially all being less than about 12 microns in diameter or (b) the alpha-alumina flakes described in Example 1, in a toothpaste formulation as described below.

The toothpastes show a percent polish recovery of 56-59 and a high percent stain removal (e.g. 76). The RDA is 93 (measured on Example 5b). In contrast, when 1% of very finely divided zirconium silicate of less than 1 micron average particle size (and of the following particle distribution: 10% below 4 microns, 99% below 2.5 microns, 94% below 2 microns, 72% below 1 micron, 46% below 0.5 micron, 27% below 0.3 micron, 3% below 0.2 micron, (Ultrox 1000W) is used in place of the alumina flakes the percent polish recovery is 58 and the percent stain removal is about 50, the RDA is 64, and the toothpaste does not have as pronounced a sparkling, pearlescent appearance.

The toothpaste formulation contains the following ingredients, in addition to those named above: glycerine 25 parts, sorbitol-water mixture (70% sorbitol 30% water) 41.8 parts, deionized water 3 parts, polyethylene glycol 3 parts, sodium lauryl sulfate 2 parts, chloroform 1 part, sodium carboxymethylcellulose 0.35 part, sodium benzoate 0.5 part, sodium saccharin 0.17 part, flavor (essential oil) 1 part, 1% aqueous solution of F D & C yellow #5 0.09 part, 1% aqueous solution of F D & C blue #1, 0.09 part. The pearlescent flakes are titanium dioxide-coated mica flakes (Timica Sparkle), ranging in size from about 15-40 microns; their thickness is about 0.7 microns; their titanium dioxide coatings (on both faces of each flake) are of anatase; and their composition is about 20% anatase, 80% mica. The polyethylene glycol has an average molecular weight of about 600. The low density silica gel has a bulk density of about 0.11 g/cm$^3$, a particle size of about 4 microns, a surface area of 310 m$^2$/g, an oil absorption value of about 310 g/100g and a pH (for a 5% aqueous slurry) of 7.6.

EXAMPLE 6

Example 5b is repeated except that the sodium aluminosilicate has the following empirical composition: -silica about 78%' alumina about 1%; sodium oxide about 10%, water (determined by loss on ignition at 1000° C) about 10%. It has a surface area of about 225-300 m$^2$/g an oil absorption of about 80-110 g/100 g, a particle size of about 2 to 4 microns and a pH (measured on a 4% slurry in water) 7.5. The toothpaste shows a percent polish recovery of 57 and a percent stain removal of 84.

EXAMPLE 7

Example 5b is repeated except that the amount of the aluminosilicate is increased 27%, the low density silica gel is omitted and the amount of sorbitol-wash mixture is decreased to 35 parts.

EXAMPLE 8

(a) A toothpaste is prepared contianing 47% hydrated alumina (dental grade, of average particle size about 9 microns) and 5% of the alpha-alumina flakes described in Example 1, in a dental vehicle (b) Example 8a is repeated except that the amount of hydrated alumina is reduced to 42% and the amount of the alpha-alumina is increased to 10%.

(c) Example 8a is repeated, except that the amount of hydrated alumina is increased to 52% and the alpha-alumina is omitted. In all cases the RDA is within the range of 230-260.

EXAMPLE 9

A toothpaste having a gritty feel is prepared containing 20% hydrated alumina (average particle size 40 microns), 23% polyvinyl chloride particles (average particle size about 15 microns), 2% of the alpha-alumina flakes described in Example 1, glycerine 22%; sodium carboxymethyl cellulose 0.85%; sodium benzoate 0.50%; sodium saccharin 0.20%; sodium lauryl sulfate, 0.975%; 35% aqueous solution of sodium N-lauroyl sarcosinate 2.00%; chloroform 3.30%; flavoring oil 1.30%; deionized water, 23.675%, corrosion inhibitor 0.2%.

EXAMPLE 10

A toothpaste is prepared containing 44% calcium pyrophosphate (dental grade, average diameter about 7 to 8 microns) and 2% of the alpha-alumina flakes described in Example 1, together with the following ingredients: glycerine 26%; sodium carboxymethyl cellulose 1.10%; sodium benzoate 0.50%; sodium saccharin 0.20%; sodium lauryl sulfate, 0.975%; 35% aqueous solution of sodium N-lauroyl sarcosinate 2.00%; chloroform 3.30%; flavoring oil 1.30%; titanium dioxide pigment 0.2%; deionized water (containing a small amount of corrosion inhibitor), balance. The RDA is 473, the percent repolish is 50, and the percent stain removal is 90.

EXAMPLE 11

A toothpaste is prepared according to the following formulation:

|  | Percent by Weight |
| --- | --- |
| Glycerine | 22.00 |
| Water | 28.24 |
| Polyvinyl chloride (of about 15 microns average particle size) | 43.00 |
| Alpha alumina flakes (described in Ex. 1) | 2.00 |
| Sodium carboxymethylcellulose | 1.00 |
| Sodium benzoate | 0.50 |
| Sodium lauryl sulfate | 1.50 |
| Sodium saccharine | 0.20 |
| Sodium monofluorophosphate | 0.76 |
| Flavor | 0.80 |

EXAMPLE 12

The alpha-alumina flakes may be included in a toothpaste containing particles of baking soda, as the major proportion of the abrasive by weight (e.g. about 25-60% of the toothpaste). One such toothpaste has the following composition:

40% baking soda powder, 5% alpha alumina flakes of Example 1, 0.4% titanium dioxide, 33.4% glycerol, 15.18% deionized water, 1.1% CMC (Hercules 7MF), 2% of a solution of 35% sodium N-lauroyl sarcosinate in a mixture of 35% water and 30% glycerol, 1% sodium lauryl sulfate, 1% flavor (water-insoluble essential oil flavoring agent, e.g. essential oil mixture rich in peppermint oil), 0.5% sodium benzoate and 0.2% sodium saccharin, and 0.22% sodium fluoride.

The baking soda powder is U.S.P. grade having the following particle size distribution in which percentages represent the cumulative percent retained on the named sieve, and sieve sizes are U.S. Standard: #45 sieve, trace; #70 sieve (sieve opening 210 microns), 27%; #80 sieve (sieve opening 177 microns) 66.5%, #100 sieve (sieve opening 149 microns), 92.5%; #170 sieve (sieve opening 88 microns), 99%.

The titanium dioxide used is a grit-free anatase powder at least 99.0% of which passes through a #325 U.S. Standard sieve and whose mean particle diameter (as measured on a Kahn sedimentation balance) is below 1 micron. Microscopic measurements indicate its average particle diameter is 0.3 micron.

The toothpaste has good cleaning power and whiteness and ages well. It shows very good resistance to flavor separation on aging and very good retention of fluoride content. Its percent repolish is 64%. Because of the relatively large particle size of the baking soda a ribbon of the toothpaste, extruded from its tube, has a finely textured grainy appearance to the naked eye. The toothpaste has a pleasant feel during brushing; while the large particles of baking soda are palpable they break down to smaller particles easily under the pressure of the toothbrush and under the action of the saliva.

While it is most preferred to use alumina flakes whose mean particle diameter is less than five microns (e.g. about 3 to 4 microns) it is within the broader scope of this invention to use alumina flakes of larger diameters but similar thickness, such as alumina flakes, described in the aforesaid U.S. Pat. No. 3,121,623 having average diameters of 9, 12 or 15 or more microns, free of particles over 40 microns in diameter (preferably free of particles over about 20 microns in diameter) and substantially free of particles having thicknesses above about 3 microns.

EXAMPLE 13

A toothpaste is prepared containing 24% of the sodium aluminosilicate particles of Example 6, and 10% of the alpha-alumina flakes described in Example 1, together with 25% glycerine; 1.2% sodium carboxymethyl cellulose; 0.5% sodium benzoate; 0.2% sodium saccharine; 0.4% $TiO_2$; 1.5% sodium lauryl sulfate.

In a preferred form of the invention the alpha-alumina flakes are uncoated and free of adhesion to particles of other materials.

In a stain removal test, sections of human dental enamel are etched with 0.1N HCl for 2 minutes, rinsed with water, then wet with a dilute solution of stannous fluoride, wiped dry, and finally exposed to a stream of hydrogen sulfide gas which results in the deposition of a brown deposit of stannous sulfide. The amount of stain on the surface is measured with a Gardner Automatic Color Difference meter. The surface is then brushed with a mechanical brushing machine for 3000 reciprocal strokes with a slurry of a dentifrice and the residual stain measured with the meter. Finally, the stain which remains is completely removed with dental pumice and the reflectance of this surface is read. The ability of a dentifrice to remove the stain is expressed by the following equation.

$$\text{Percent Stain removed} = \frac{(Rd_{3000\ strokes} - Rd_{initial}) 100}{Rd_{pumiced} - Rd_{initial}}$$

where $Rd$ initial, $Rd$ 3000 strokes, and $Rd$ pumiced are respectively the reflectance values measured on the initially stained surfaces, after brushing for 3000 reciprocal strokes and after removing the residual stain by pumicing.

The percent repolish is determined by a test in which sections of human dental enamel, upon which have been ground flat areas, are first polished, then dulled with chalk, and then brushed with a slurry of a dentifrice for 5000 reciprocal strokes. A "Monsanto Tooth Reflectance Instrument" is employed to measure the specular reflectance of the surface after each step described above. The dulled surface is adjusted so that it is approximately 150 units (Monsanto Instrument) lower than the polished surface. The polishing ability of the dentifrice is expressed by Equation 2.

$$\text{Percent Repolish} = \frac{(SR_{5000\ strokes} - SR_{dulled})100}{SR_{polished} - SR_{dulled}} \quad \text{(Equation 2)}$$

Where $SR$polished, $SR$dulled and $SR$5000 strokes are respectively the specular reflectance values of the enamel surface after the initial polishing, after dulling with chalk, and after brushing with a dentifrice slurry.

The RDA values are obtained by a procedure based on a radioactive technique described in the literature; Stookey, C. K. and Muhler, J. C., J. Dental Research 47 524 – 538 (1968).

It is also within the broader scope of the invention to include other alpha-aluminas, or other abrasives of Mohs hardness above 6, in admixture with the alpha-alumina flakes. For instance, in Example 1, one may replace about one half of the alumina flakes by a pulverized alpha-alumina of irregular shape and having a mean particle size of about 3 to 4 microns (with all said irregular particles being less than about 7 microns in their largest dimension); thus, the toothpaste may contain, say, 3% of the flakes and 2% of said irregular particles.

While the alpha-alumina flakes have proved most useful thus far in toothpaste, they may also be similarly incorporated into toothpowders or into dental creams which are of pourable consistency.

The pH of the dentifrices is generally within the range of about 4 to 10, e.g. about 5 to 8.

Reference is made herein to the copending application of Colodney and Cordon entitled "Dental Polishing Creams", filed on Apr. 30, 1973 as Ser. No. 355,372 and which is now U.S. Pat. 3,954,961, issued May 18, 1976, whose entire disclosure is incorporated herein by reference.

The particle diameters given in the Examples are determined by conventional methods. Thus the standard liquid sedimentation technique may be used. The calculation of particle diameter from the sedimentation data being made (as is conventional) on the basis of Stokes' Law, disregarding the particular shape of the particles.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A dentifrice comprising, as an abrasive, alpha-alumina which is in the form of flat flakes having an average diameter of less than about 20 microns and thicknesses of less than about 3 microns, the proportion of said alpha-alumina being above about 0.1% and less than about 60% of said dentifrice, said alpha-alumina being a component of visible agglomerated particles of a thermoplastic resin having a molecular weight between about 1000 and 100,000, said visible agglomerated particles being in the range of about 0.5 to 50 microns in size and dispersed in said dentifrice in amount of up to about 60% by weight.

2. A dentifrice as in claim 1 in which said flakes have an average diameter of less than about 7 microns.

3. A dentifrice as in claim 2 in which said average diameter is in the range of about 2 to 7 microns.

4. The dentifrice claimed in claim 1 wherein said visible agglomerated particles are about 150–450 microns in size, contain about 80% of said alpha-alumina flakes and about 20% of polyethylene having a molecular weight of about 1500 and said flakes have a mean particle diameter of about 5 microns with substantially all of said particles being less than about 12 microns in size.

5. The dentifrice claimed in claim 4 wherein said visible agglomerated particles are present in amount of about 2% by weight of said dentifrice.

* * * * *